United States Patent [19]
Pittaro et al.

[11] Patent Number: 5,341,206
[45] Date of Patent: Aug. 23, 1994

[54] METHOD FOR CALIBRATING A SPECTROGRAPH FOR GASEOUS SAMPLES

[75] Inventors: Richard J. Pittaro, San Carlos; Tad D. Simons, Palo Alto, both of Calif.

[73] Assignee: Hewlett-Packard Company, Palo Alto, Calif.

[21] Appl. No.: 984,812

[22] Filed: Dec. 3, 1992

[51] Int. Cl.$^5$ .................. G01J 3/44; G01N 21/65
[52] U.S. Cl. ........................... 356/301; 250/252.1
[58] Field of Search .............. 356/301, 307; 250/252.1 A

[56] References Cited

U.S. PATENT DOCUMENTS

| | | | |
|---|---|---|---|
| 3,728,540 | 4/1973 | Todd et al. | 356/51 |
| 4,648,714 | 3/1987 | Benner et al. | 356/301 |
| 4,692,621 | 9/1987 | Passaro et al. | 250/252.1 A |
| 4,784,486 | 11/1988 | Van Wagenen et al. | 356/301 |

*Primary Examiner*—F. L. Evans

[57] ABSTRACT

A method for field calibrating a system adapted for spectrographic analysis of gaseous substances. The method uses an easily available gas, for example ambient air, thereby providing for field calibration of the system without the inconvenience of using a purified noble gas and a pre-measured calibration gas mixture. During calibration, spectrograms from the easily available gas are generated by the system at various number density levels of the gas. Information from the spectrograms is then used in setting an operating parameter of the system.

20 Claims, 10 Drawing Sheets

DARK SIGNAL
(Without laser power)

Dark Signal

BACKGROUND SIGNAL
(With dark signal eliminated)

Background Signal

METHOD FOR CALIBRATING A SPECTROGRAPH FOR GASEOUS SAMPLES

BACKGROUND

The present invention is generally directed to a calibration method, and more particularly to a method for calibrating a system adapted for spectrographic analysis of gaseous substances.

Instrumentation that analyzes gaseous substances is required in a variety of important applications. For example, during a surgical operation, patients are anesthetized through the careful administration of gases such as nitrous oxide. The supply of these anesthetics must be regulated with great precision. In addition, the gases expelled in the patient's breath need to be monitored continuously to determine the condition of the patient. Instrumentation that analyzes gasses exhaled by patients provide vital information to surgical personnel. Field calibration of such instrumentation maintains its accuracy while maximizing its availability for operating room procedures.

A particular class of instrumentation employs Raman spectroscopy to detect the presence and concentration of gaseous substances. Scattering of light by the Raman effect has received much attention from scientists since its original exposition by C. V. Raman in 1928. Instrumentation that employs the Raman effect provides a light, such as a laser beam, which illuminates molecules of a gas disposed within a sampling cell. Molecular vibrations of the gas cause the light to scatter off the illuminated gas molecules to produce scattered light in a process which shifts the frequency of the scattered light by exactly the vibrational frequency of the molecule. More generally, the scattered light comprises a spectral signal generated by stimulating the gas with the light. The frequency shift of the spectral signal is characteristic of the gas being analyzed and is independent of the frequency of the illuminating light. Thus, measurement of the spectral signal can be used to infer properties of the gas being analyzed, such as chemical composition and concentration. The spectral signal is collected from the gas disposed within the sampling cell and the constituent frequency components of the spectral signal are analyzed. The analyzed frequency components are used to produce a spectrogram, which can be displayed on a display device. By interpreting the spectrogram, the presence and concentration of different types of constituent gas molecules in the gas can be deduced.

Instrumentation that employs the Raman effect is described in U.S. Pat. No. 4,648,714 entitled "Molecular Gas Analysis By Raman Scattering in Intracavity Laser Configuration" by Benner et al. issued Mar. 10, 1987, and in U.S. Pat. No. 4,784,486 entitled "Multichannel Molecular Gas Analysis By Laser-Activated Raman Light Scattering" by Van Wagenen et al. Because each of these patents provide helpful background information, they are incorporated herein by reference. The instrumentation described in each of these two patents provides a laser beam that illuminates molecules of a gas disposed within a sampling cell. Raman scattered light generated by the Raman-effect is collected from the gas disposed within the sampling cell. Each patent focusses on a respective means for detecting constituent frequency components of the Raman scattered light. As disclosed in each patent, a microprocessor coupled to the detection means receives electrical signals representative of the constituent frequency components of the Raman scattered light. Results are displayed on a display controlled by the microprocessor.

It should be briefly noted that although it is possible to display a given spectrogram in any one of a variety of different formats, the substance of fundamental calibration requirements discussed herein remains, regardless of display format. The fundamental calibration requirements discussed herein can be suitably translated for each different format. For the sake of clarity, a common spectrogram format is discussed herein. For each type of constituent gas molecules, the spectrogram displays a single vertical spectral peak or several vertical spectral peaks located along a horizontal axis of the spectrogram. Location of spectral peaks along the horizontal axis of the spectrogram is determined by the amount that the frequency of the spectral signal is shifted from the frequency of the illuminating light. The amount of frequency shift is scaled by the speed of light and displayed along the horizontal axis of the spectrogram as a wave number offset. Location or "height" of spectral peaks along the vertical axis of the spectrogram corresponds to relative intensity of the spectral peaks. Relative intensity of the spectral peaks is determined by the respective relative concentration of each different type of constituent gas molecule.

As discussed herein, there are fundamental requirements for field calibration of instrumentation for Raman spectroscopy. A first field calibration requirement is to correctly scale spectrograms displayed by the instrumentation. This first calibration requirement includes displaying spectral peaks of any given spectrogram at correct relative intensity locations along a vertical axis of the given spectrogram. This first calibration requirement further includes displaying spectral peaks of the given spectrogram at correct frequency locations along a horizontal axis of the given spectrogram. For example, it is expected that a spectrogram of nitrous oxide, $N_2O$, produced by properly calibrated instrumentation should display spectral peaks located along the horizontal axis of the spectrogram at wave number offsets of 1285 and 2224 $cm^{-1}$. To be effective, a calibration method should operate over a broad range of frequencies.

A bottle of a pre-measured calibration gas mixture containing a wide range of constituent gasses at pre-measured concentrations is useful in satisfying this first requirement. During field calibration, the bottle is opened and the gas mixture is released into the sampling cell for analysis. The instrumentation produces a spectrogram having a wide range of spectral peaks due to the wide range of constituent gasses. Since the identity of the constituent gasses disposed within in the bottle is already determined, correct frequency locations of spectral peaks in the spectrogram of such gasses is already determined. The correct frequency locations are used to align the frequency locations of measured spectral peaks along the horizontal axis of the spectrogram. Since concentrations of constituent gasses disposed in the bottle are already determined, correct relative intensity levels for spectral peaks in the spectrogram of such gasses are already determined. The correct relative intensity levels are used to adjust intensity gain of the instrumentation with respect to the measured relative intensity levels of the spectral peaks.

A second field calibration requirement is to reduce negative effects of collateral scattering on the spectrograms displayed by the instrumentation. Though the phenomenon of collateral scattering is not fully understood, it is theorized that collateral scattering takes place when the light source which illuminates molecules of the gas being analyzed also illuminates other materials adjacent to the gas, thereby causing the adjacent materials to scatter the light or to fluoresce. Such light from the adjacent materials is undesirable and is referred to herein as collateral scattered light. It is theorized that the spectral signal, comprising desired fight scattered from the gas being analyzed, becomes intermixed with the collateral scattered light. This intermixing degrades the spectral signal collected by the instrumentation, which in turn obscures the spectrograms displayed by the instrumentation.

A bottle of a purified noble gas, such as purified Argon, is useful in satisfying this second field calibration requirement. During field calibration, the bottle of noble gas is opened and the noble gas is released into the sampling cell for analysis. It is theorized that only light from the adjacent materials is collected because noble gasses do not exhibit Raman scattering. Accordingly, the instrumentation generates a background signal spectrogram that is representative of the collateral scattered light. The background signal spectrogram is then used to reduce the negative effects of collateral scattering on the spectrograms displayed by the instrumentation.

As discussed, specialized calibration gasses such as the purified noble gasses and the pre-measured calibration gas mixture are useful in calibration. However such specialized calibration gasses also have disadvantages. For example, completing calibration using these gasses naturally requires availability of both the bottle of noble gas and the bottle of pre-measured gas mixture. Since analysis of the noble gas does not produce a spectrogram that is useful in frequency location alignment or gain calibration, the pre-measured gas mixture would be needed to complete calibration. Similarly, since analysis of the pre-measured calibration gas mixture produces a spectrogram having numerous spectral peaks that obscure the background signal spectrogram, the noble gas would be needed to complete calibration. By this reasoning, a hospital organization that performs field calibration would need to maintain a supply of bottles of pre-measured calibration gas mixture as well as a supply of bottles of purified noble gas.

Every item stored and dispensed by a hospital for a patient's surgery directly or indirectly adds to the cost of the surgical procedure. Skyrocketing health care costs require simplification and streamlining of medical procedures, while maintaining high quality care. While field calibration is needed to maintain the integrity of spectrographic measurements, the use of specialized calibration gasses adds to cost and complexity of field calibration procedures. A new field calibration method is needed that satisfies the field calibration requirements while eliminating the expense and inconvenience of specialized calibration gasses.

SUMMARY OF THE INVENTION

The present invention provides an efficient method for calibrating a system adapted for spectrographic analysis of gaseous substances. A novel calibration method using an easily available gas, for example ambient air, provides for field calibration of the system without need for premeasured bottles of specialized calibration gasses. Furthermore, by generating spectrograms from the easily available gas at various number density levels of the gas, the method of the present invention completes field calibration of the system without the expense and inconvenience associated with methods that employ purified samples of noble gases.

Briefly and in general terms, a preferred embodiment of the present invention uses the system under field calibration to generate a spectrogram from ambient air. Spectral data stored in the system during factory calibration is retrieved. In particular, the spectral data includes oxygen spectral data and nitrogen spectral data. The spectrogram of ambient air and the retrieved spectral data are used in setting an operating parameter of the system.

Another aspect of the present invention is not necessarily limited to ambient air, but is practiced in alternative embodiments with virtually any available gas, with beneficial results. A first spectrogram is generated from the gas at a first number density level. The first number density level of the gas is then changed to a second number density level. A second spectrogram is generated from the gas at the second number density level. The first and second spectrogram are used in generating a background signal spectrogram. The background signal spectrogram is then included in the operating parameter of the system.

The present invention provides a novel field calibration method that eliminates the expense and inconvenience of specialized calibration gasses. Other aspects and advantages of the present invention will become apparent from the following detailed description, taken in conjunction with the accompanying drawings, illustrating by way of example the principles of the invention.

DETAILED DESCRIPTION OF THE INVENTION

Figure 1:
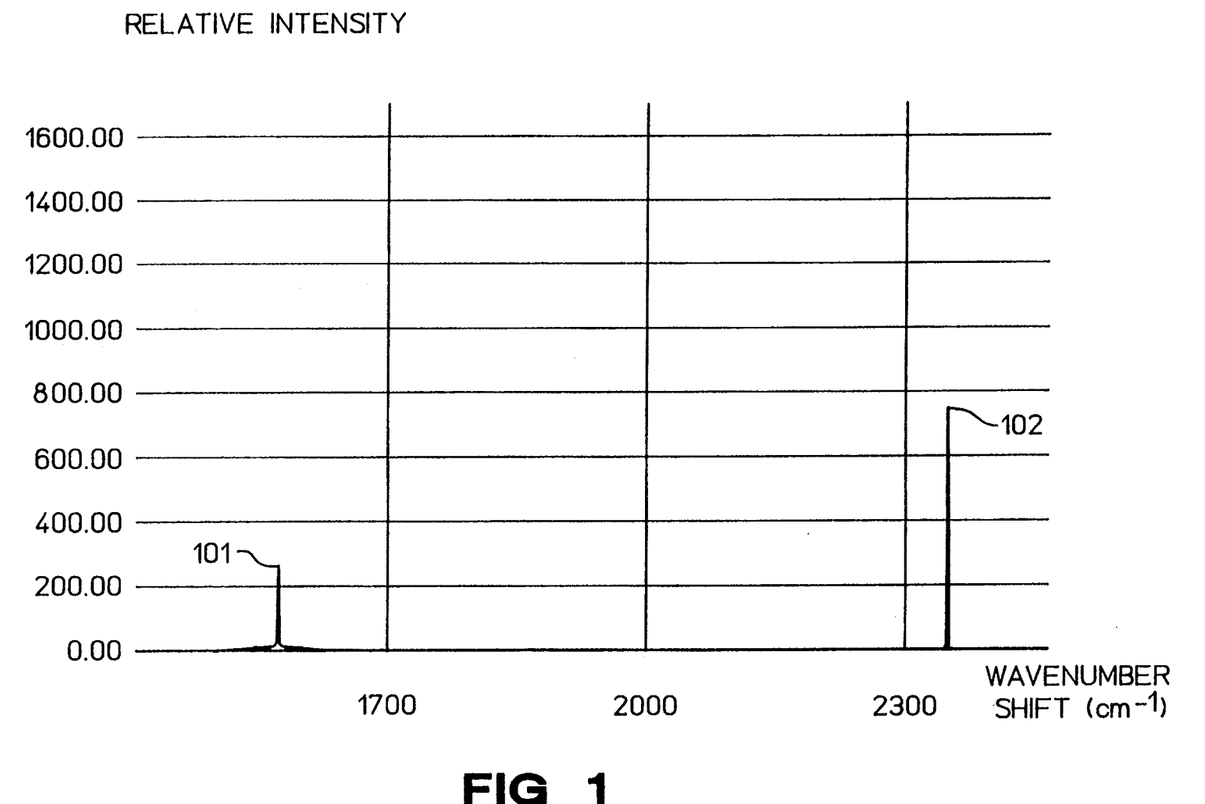
FIG. 1 is a graphical view of a spectrogram of ambient air at a pressure of 1 atmosphere.

As shown in the exemplary drawings, the invention is embodied in a method for calibrating a system adapted for spectrographic analysis of gaseous substances. One of the novel aspects of a preferred embodiment of the present invention is that a spectrogram of ambient air is generated and used in system calibration, thereby eliminating need to use specialized calibration gasses that add additional cost and inconvenience. It should be noted that principle components of ambient air are oxygen, $O_2$, and nitrogen, $N_2$. A Raman spectrogram of ambient air produced by a properly calibrated system should display spectral peaks located along the horizontal axis of the spectrogram at wave number offsets of 1555 $cm^{-1}$ and 2331 $cm^{-1}$, each of the locations respectively corresponding to $O_2$ and $N_2$. FIG. 1 shows a spectrogram generated by a correctly calibrated system from a sample of ambient air at standard temperature and a pressure of 1 atmosphere. In particular, the spectrogram of FIG. 1 illustrates the respective spectral peaks associated with oxygen 101 and nitrogen 102. As will be explained in greater detail later herein, in a preferred embodiment of the present invention a spectrogram of ambient air is generated and used in calibration, wherein the two spectral peaks provided by oxygen and nitrogen are particularly useful as calibration points.

As shown in FIG. 1 the respective spectral peaks of oxygen and nitrogen are separated by a broad frequency range. The respective spectral peaks of oxygen and nitrogen are especially useful as calibration points because they are separated by the broad frequency range. In accordance with principles of the present invention, using air in calibration is an effective choice because spectrograms of air provide a broad useful calibration range between spectral peaks used as calibration points. Since ambient air is conveniently available for field calibration of the system, there is no need for field calibration personnel to use and maintain a supply of specialized calibration gasses.

Another novel aspect of the present invention is generating spectrograms from a conveniently available calibration gas, such as ambient air, at various number density levels of the gas. As explained in greater detail later herein, these spectrograms are used in generating a background signal spectrogram. The method of the present invention provides for field calibration of the system without using purified samples of noble gasses, such as purified Argon, that would alternatively be used in generating the background signal spectrogram.

Figure 2:
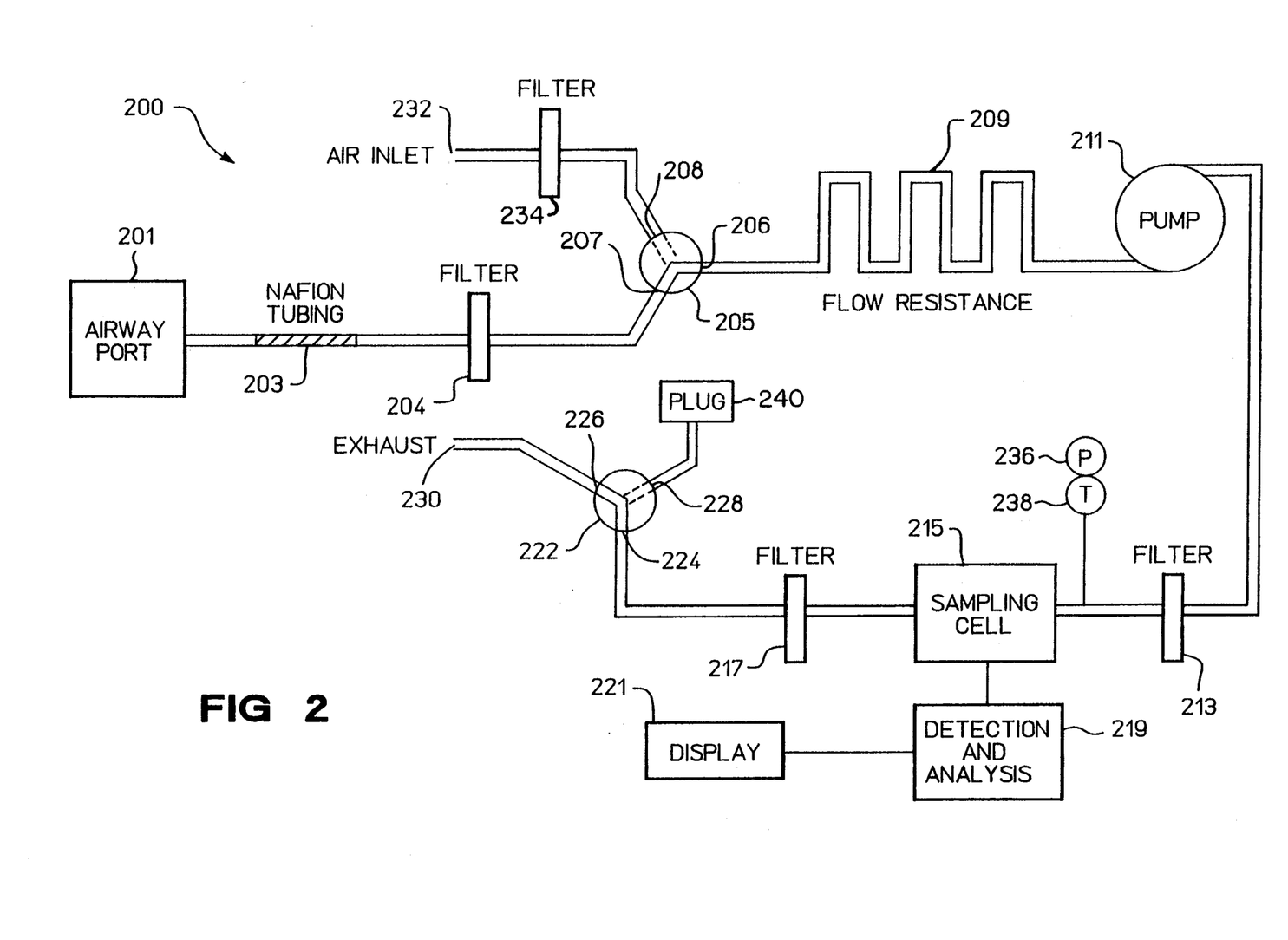
FIG. 2. is a block diagram of a preferred spectrographic analysis system used in conjunction with a preferred embodiment of a method of the present invention.

The principles of the invention will be further illustrated using a block diagram as shown in FIG. 2. The block diagram shows a spectrographic analysis system 200 used in conjunction with the preferred embodiment of the calibration method of the present invention. During normal operation of the spectrographic analysis system, an airway port 201 conducts a flow of breath, exhaled by a surgical patient, into the system. The flow of breath passes through a length of tubing 203, which is permeable to water vapor and coupled to the airway port. It is known that tubing sold under the registered trademark "Nafion" provides water vapor permeability. It should be understood that though embodiments of spectrographic analysis systems are described herein as employing Nafion tubing, this should not be construed as limiting the present invention.

In order to substantially remove moisture in the breath that would otherwise degrade Raman spectroscopy of anesthetic gasses, it is preferred that the length of Nafion tubing 203 be between 30 and 60 centimeters in length. A first filter 204 is coupled to the Nafion tubing. It should be briefly noted that since the Raman-effect is particularly sensitive to particles suspended in the breath, filters are used in the system to remove such particles.

A first valve 205 has an outlet 206 and a pair of alternatively selectable inlets 207, 208. A first member 207 of the pair of inlets is coupled to the first filter. During normal operation, only the first member of the pair of inlets is selected, thereby conducting the flow of breath into the system and through the first valve. The outlet 206 of the first valve is coupled to a flow resistance device 209.

A pump 211 is coupled to the flow resistance device so as to draw the flow of breath through the system. The amount of flow resistance provided by the flow resistance device is selected to maximize the efficiency of the pump, as the pump draws breath through the system. Alternatively, the flow resistance device can be omitted and the pump coupled directly to the outlet of the first valve. A second filter 213 coupled to the pump provides further filtering of the flow of breath.

A chamber 215 of a sampling cell is coupled between the second filter and a third filter 217. The flow of breath is received by the chamber of the sampling cell and analyzed by employing the Raman-effect. The pump draws the flow of breath through the system, and specifically through the chamber of the sampling cell.

In the preferred embodiment, the chamber is realized by a cylindrical waveguide. More specifically, the cylindrical waveguide is a hollow tube having a reflective inner surface. It should be understood that while it is preferred that the chamber is realized by a cylindrical waveguide, the present invention may also be practiced with beneficial results when the chamber of the sampling cell is formed by some other structure.

A laser (not shown in FIG. 2) is optically coupled to the chamber so that a laser beam from the laser illuminates constituent molecules of breath disposed within the chamber by the flow of breath though the chamber. Molecular vibrations of the gas cause light of the laser beam to scatter off the illuminated gas molecules to produce scattered light in a process which shifts the frequency of the scattered light by exactly the vibrational frequency of the molecule. More generally, the scattered light comprises a spectral signal generated by stimulating the gas with the laser beam. The frequency shift of the spectral signal is characteristic of the gas being analyzed and is independent of the frequency of the illuminating laser beam. As discussed later herein, the spectral signal from the constituent gasses are used to infer properties of constituent gasses of the breath, such as chemical composition and concentration. It should be understood that while it is preferred to use intense light of the laser beam to stimulate the gas, the calibration method of the present invention produces beneficial results when alternative ways of stimulating the gas are used, for example using a less intense conventional light source.

The analysis system includes a detection and analysis portion 219 for detecting and analyzing constituent frequency components of the spectral signal. The detection and analysis portion 219 is optically coupled to the chamber 215, by means of collection optics, for receiving the spectral signal from the chamber. The detection and analysis portion is essentially a spectrometer which includes, for example, a diffraction grating optically coupled to a photosensor array, and a computation means electrically coupled to the photosensor array. In the preferred embodiment the computation means includes a microprocessor coupled to a suitable memory device and programmed to generate a spectrogram. It should be understood that though embodiments of spectrographic analysis systems are described herein as employing a particular spectrometer architecture, this should not be construed as limiting the present invention.

In the preferred embodiment, the spectral signal is collected from the chamber by the collection optics and imaged onto the diffraction grating. The diffraction grating separates constituent frequency components of the spectral signal. The photosensor array is positioned adjacent to the diffraction grating for detecting the separated frequency components of the spectral signal. In response to the frequency components of the spectral signal, the photosensor array produces electrical signals, which the computation means uses to produce a spectrogram of the breath. Chemical composition and concentration of constituent gasses of the breath can then be inferred from the spectrogram. In the preferred embodiment, the detection and analysis portion of the system is coupled to a display device 221 for displaying the spectrogram.

From the sampling cell 215, the breath flow continues through the third filter 217, which is coupled to the sampling cell. A second valve 222 shown in FIG. 2 has an inlet 224 and a pair of alternatively selectable outlets 226, 228. The inlet 224 is coupled to the third filter.

A first member 226 of the pair of outlets is coupled to an exhaust 230 of the system. During normal operation, only the first member of the pair of outlets is selected, thereby conducting the flow of breath from the third filter, through the second valve, and out of the system through the exhaust.

Figure 3:
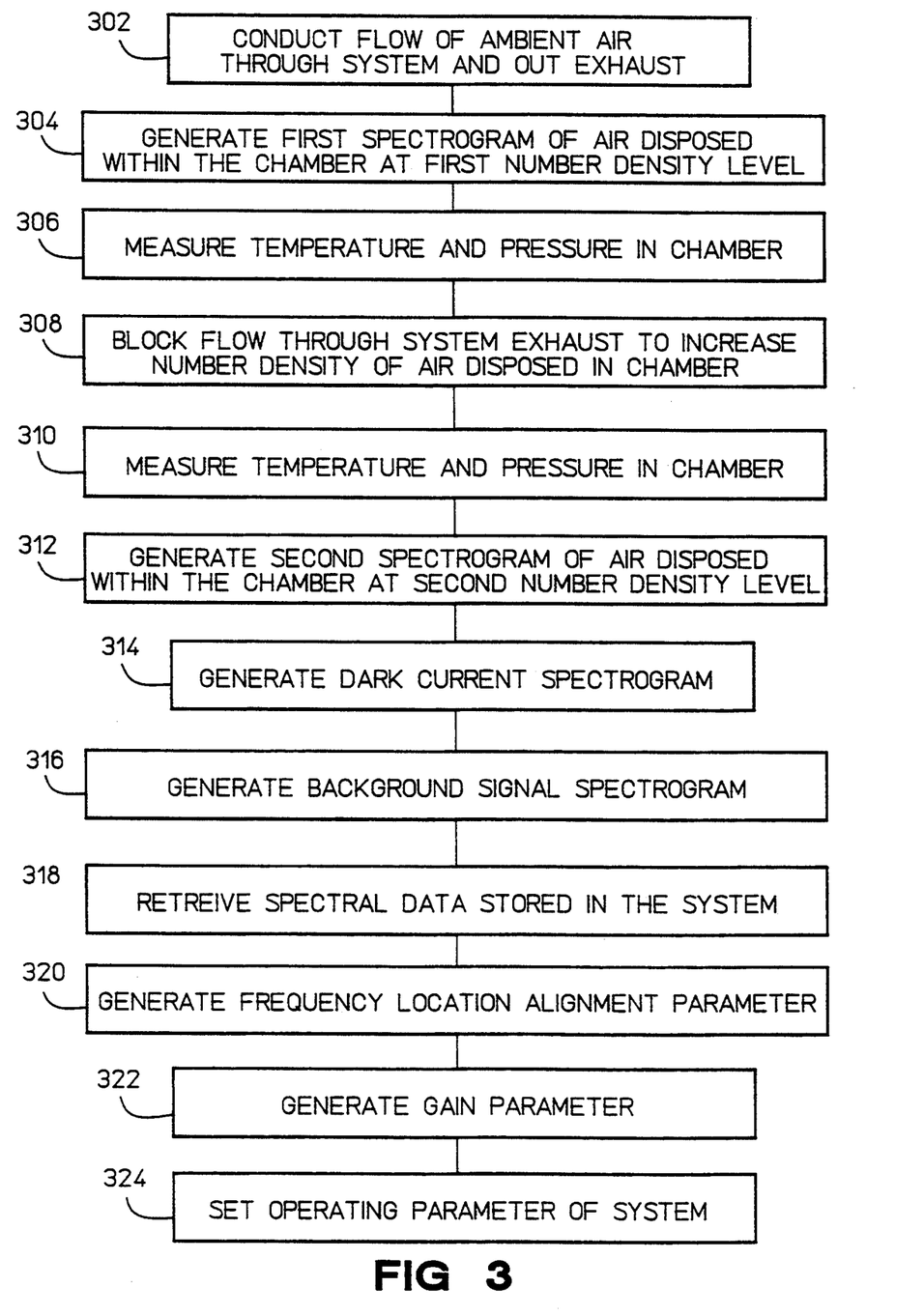
FIG. 3 is a flow chart shown illustrating a preferred embodiment of the method of the present invention.

In order to prepare the system for normal operation as discussed, a field calibration is performed according to the calibration method of the present invention. A flow chart shown in FIG. 3 illustrates a preferred embodiment of the calibration method of the present invention. In accordance with block 302 of the flow chart, ambient air is conducted through the analysis system and out the exhaust. This is easily illustrated using the block diagram of FIG. 2.

As shown in FIG. 2, ambient air is collected through an ambient air inlet 232, which is coupled to a fourth filter 234. The fourth filter is coupled to a second member 208 of the pair of inlets of the first valve 205. During field calibration, only the second member of the pair of inlets of the first valve is selected, thereby conducting only a flow of ambient air into the system. Accordingly, the ambient air flows from the ambient air inlet 232, through the fourth filter 234, through the first valve 205, to the flow resistance device 209. As with the flow of breath discussed previously, the pump 211 draws the flow of ambient air through the flow resistance device, and eventually through the chamber of the sampling cell.

As the ambient air flows through the chamber of the sampling cell, the ambient air is disposed within the chamber 215 of the sampling cell at a first number density level. The first member 226 of the pair of outlets of the second valve 222 is selected, thereby conducting the flow of ambient air out of the system through the exhaust 230.

In a similar manner as discussed previously with respect to breath disposed within the chamber, the Raman-effect is employed to generate a spectral signal from the air disposed within the chamber at the first number density level. The laser beam illuminates the ambient air, thereby generating a spectral signal from the air by the Raman-effect. The spectral signal is then collected from the chamber by the collection optics and analyzed by the detection and analysis portion of the system to produce a first measured spectrogram of air disposed within the chamber at the first number density level, consistent with block 304 of the flow chart in FIG. 3.

It is desired to reduce effects of collateral scattering phenomena through calibration. Though the phenomenon of collateral scattering is not fully understood, it is theorized that collateral scattering takes place when the laser beam which illuminates molecules of the gas within the chamber also illuminates materials of the chamber which are adjacent to the gas. It is theorized that this illumination causes the adjacent materials to scatter the laser beam or to fluoresce. Such light from the adjacent materials is undesirable and is referred to herein as collateral scattered light. It is theorized that the spectral signal, comprising desired light scattered from the gas being analyzed, becomes intermixed with the collateral scattered light. This intermixing degrades the spectral signal collected by the system, which in turn obscures spectrographic measurements of the system.

It should be noted that both laser power level and number density level effect Raman spectrographic measurements. For example, intensity of the desired spectral signal produced by the Raman effect increases as power of the illuminating laser beam increases and as number density of gas disposed within the chamber increases. Similarly, intensity of the undesired collateral scattered light increases as power of the illuminating laser beam increases. However, intensity of the undesired collateral light is substantially unaffected by changes in the number density of gas disposed within the chamber. Accordingly, in the calibration method of the present invention, both laser power level and gas number density level are considered when performing system calibration.

Figure 4:
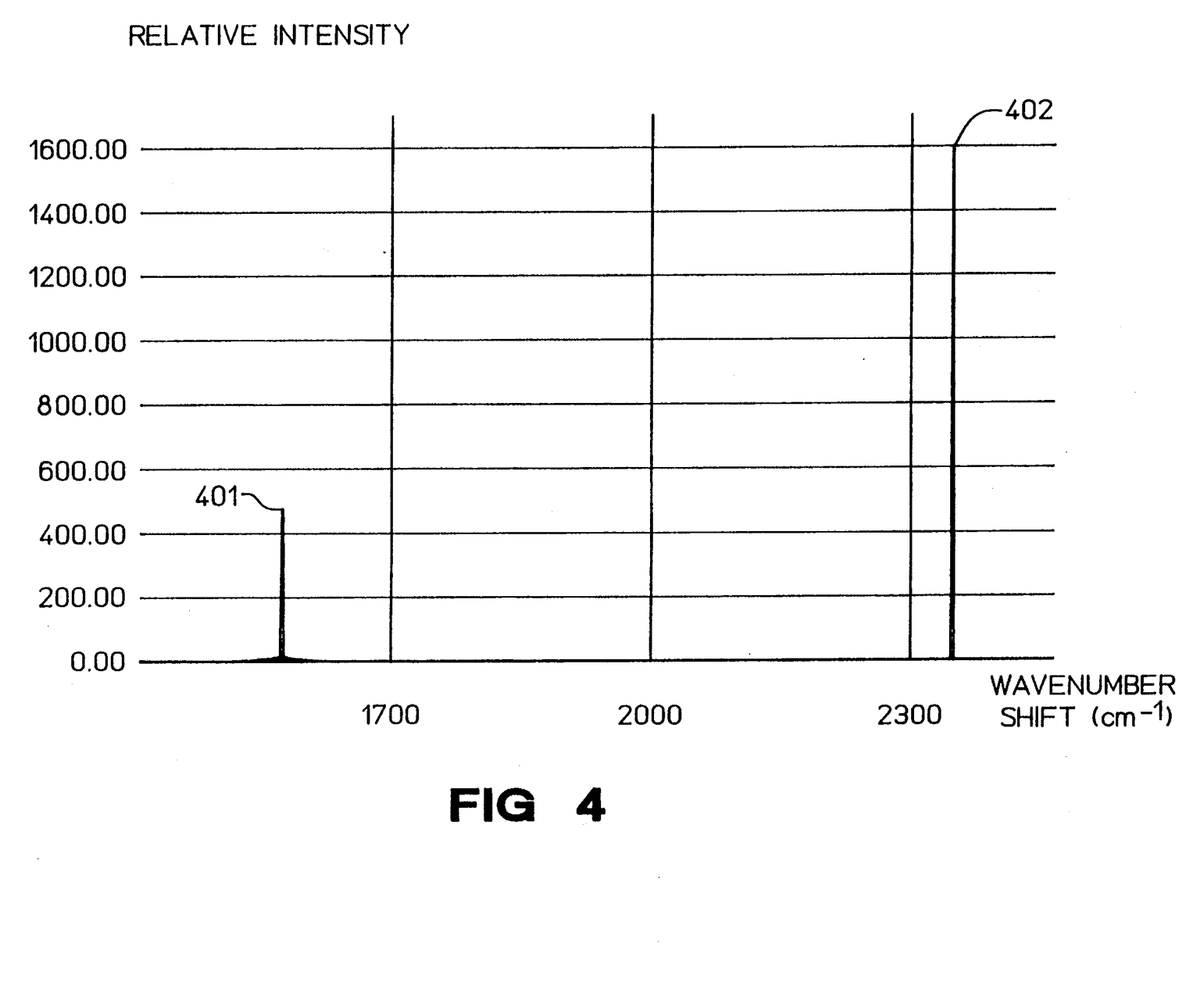
FIG. 4 is a graphical view of a spectrogram of ambient air at a pressure of 2 atmospheres.

As an illustrative example of the effect of increasing the number density of the gas disposed within the chamber, FIG. 4 shows a correctly calibrated spectrogram of air disposed within the chamber at standard temperature and a pressure of 2 atmospheres. Therefore, the air used to generate the spectrogram shown in FIG. 4 is at twice the number density level of the air used to generate the calibrated spectrogram shown in FIG. 1, discussed previously. It should be noted that the spectral peaks 401, 402 of FIG. 4 have twice the intensity of corresponding spectral peaks 101, 102 of FIG. 1.

The detection and analysis portion of the system further includes a power sensor optically coupled to the laser for measuring a power level value of the laser beam used during calibration. The analysis portion of the system then compares the power level value of the laser beam used during calibration to a reference laser beam power value stored in the memory, thereby producing a power level difference value. The analysis portion of the system then normalizes intensity of spectrograms generated during calibration, scaling the intensity of spectrograms generated during calibration by the power level difference value.

Figure 5A:
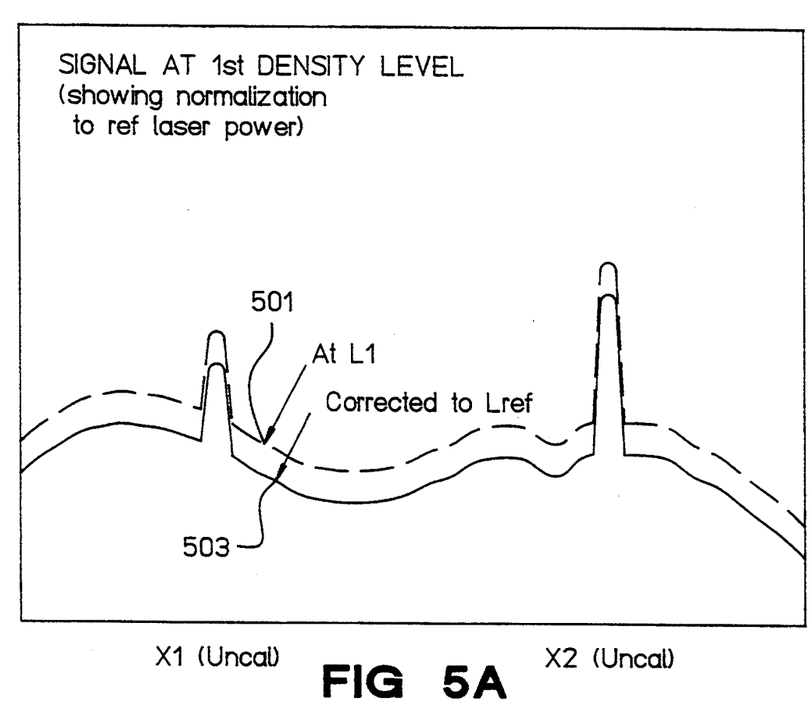
FIG. 5A is a graphical view of a first measured spectrogram and a first normalized spectrogram.

For example, FIG. 5A shows a graphical view depicting the first measured spectrogram 501 generated by the system when the ambient air disposed within the chamber at the first number density level is illuminated by the laser beam at a first laser beam power level value, L1. The detection and analysis portion of the system compares the first power level value, L1, to the reference laser beam power value, Lreff, stored in the memory, thereby producing the power level difference value. The first measured spectrogram 501 is then scaled by the power level difference value, thereby producing a first normalized spectrogram 503 of ambient air disposed within the chamber at the first number density level.

In general, number density level of a perfect gas is a measure of a number of gas molecules per unit volume occupied by the gas. Though it is often difficult to measure number density level of the gas directly, the number density level can be predicted using the ideal gas law:

$$P = nkT$$

where P is a pressure of the gas, n is the number density level of the gas, k is Boltzman's constant, and T is the temperature of the gas. The number density level of the gas is therefore predicted using a ratio of gas pressure to gas temperature.

As shown in the block diagram of FIG. 2, a cell pressure sensor 236 and a cell temperature sensor 238 are each coupled to the chamber of the sampling cell and are adapted for sensing the pressure and temperature of any gasses disposed within the chamber of the cell. In accordance with block 306 of the flow chart shown in FIG. 3, the cell pressure and temperature sensors measure the pressure and temperature of the air disposed within the chamber at the first number density level. The computation means receives these measurements of pressure and temperature and uses them in conjunction with the ideal gas law to generate a value $N_1$ which represents the first number density level.

In accordance with block 308 of the flow chart of FIG. 3, the flow of ambient air through the system exhaust is then blocked to increase number density of air disposed in the chamber. For the system illustrated in the block diagram of FIG. 2, the flow is blocked by selecting only the second member 228 of the pair of outlets of the second valve 222. A plug 240 is coupled to the second member 228 of the pair of outlets so as to block flow through the second valve 222 when the second member 228 of the pair of outlets is selected, thereby interrupting flow of ambient air out of the system.

While the flow of ambient air out the system is interrupted, the pump 211 continues to pump air into the chamber, thereby increasing the amount of air disposed within the chamber of the cell. In this way, more of the air is disposed within the chamber. Accordingly, the first number density level of air disposed within the chamber of the cell changes to a second number density level. It is preferred that the second number density level be significantly larger than the first number density level so as to reduce undesirable effects of errors inherent in the pressure sensor. For example, if a commonly available silicon pressure is used, such a sensor has an accuracy of about 0.1%. Accordingly, a 25% difference between the first and second number density levels substantially reduces undesirable effects of errors in measurements made by the silicon pressure sensor.

In accordance with block 310 of the flow chart shown in FIG. 3, the cell pressure and temperature sensors measure the pressure and temperature of the air disposed within the chamber at the second number density level. The computation means is coupled to the sensors to receive these measurements of pressure and temperature. The computation means is programmed to use the pressure and temperature measurements in conjunction with the ideal gas law to generate a value $N_2$, which represents the second number density level.

By monitoring changes in temperature and pressure, the computation means indirectly monitors changes in the number density of the air disposed within the chamber of the cell. The computation means is programmed to determine when the cell pressure and temperature sensors indirectly indicate that the density of air within the chamber is at the second number density level. At such time, the computation means is programmed to control generation of a spectral signal from the air disposed within the cell at the second number density level, in a similar manner as discussed previously with respect to air disposed within the chamber at the first number density level. In response, the detection and analysis portion of the system generates a second measured spectrogram of air disposed within the chamber at the second number density level, consistent with block 312 of FIG. 3.

Figure 5B:
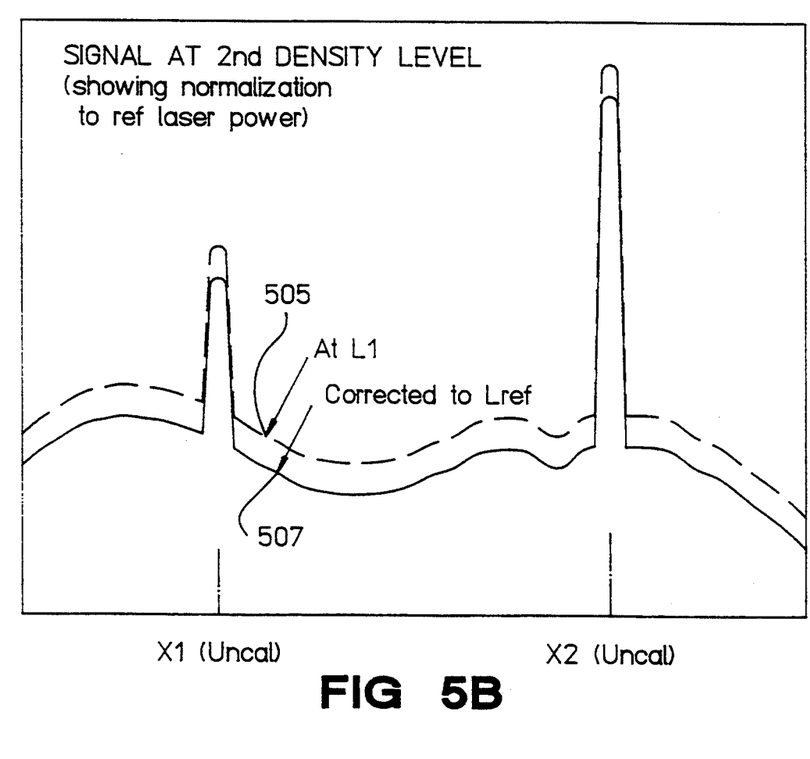
FIG. 5B is a graphical view of a second measured spectrogram and a second normalized spectrogram.

FIG. 5B shows a graphical view depicting the second measured spectrogram 505 generated by the system when the ambient air disposed with the chamber at the second number density level is illuminated by the laser beam at the first laser beam power level value, L1. In a similar manner as discussed previously, the second measured spectrogram 505 is then scaled by the power level difference value to produce a second normalized spectrogram 507 of ambient air disposed within the chamber at the second number density level.

It should be noted that if the first normalized spectrogram 503 in FIG. 5A is compared to the second normalized spectrogram 507 of FIG. 5B, it can be seen that the intensity of the spectral peaks in FIG. 5B is greater than the intensity of spectral peaks in FIG. 5A. This difference between the first and second normalized spectrograms is chiefly caused by the difference between the first and second number densities of the respective gasses used in generating each spectrogram. Since the second number density is significantly larger than the first number density, the intensity of spectral peaks in the second normalized spectrogram is significantly larger than the intensity of spectral peaks in the first normalized spectrogram.

It should be noted that, in general, a spectrogram displays relative intensity of frequency components of the spectral signal. For example, relative intensity is shown on the vertical axis of FIG. 5A and 5B, while frequency expressed as a wave number offset is shown on the horizontal axis of FIG. 5A and 5B. In FIGS. 5A and 5B the frequency locations of the spectral peaks along the horizontal axis of each of the spectrograms are shown as uncalibrated using the abbreviation "Uncal". The same abbreviation is used in FIG. 7A, discussed later herein.

Using well known vector notation, each measured spectrogram is expressed as a respective vector b having components $b_i$, which represent intensity at the ith frequency. Using this notation i takes on values that span over a range of the constituent frequency components of the spectral signal. Specifically, $b_{1i}$ represents intensity of the first normalized spectrogram at the ith frequency, and $b_{2i}$ represents intensity of the second normalized spectrogram at the ith frequency.

Figure 6A:
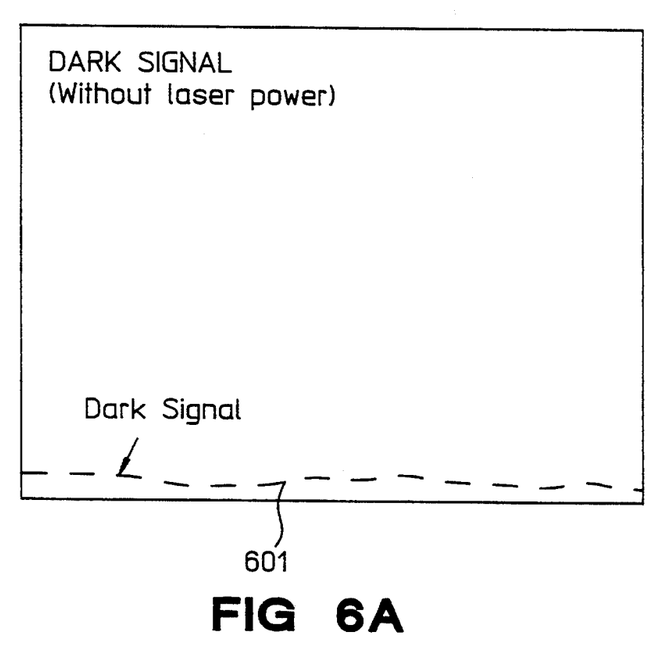
FIG. 6A is a graphical view of a dark signal spectrogram.
Figure 6B:
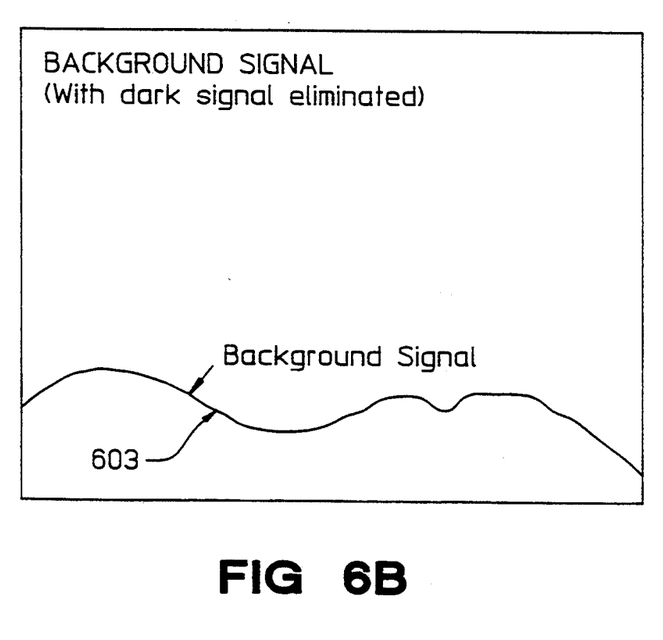
FIG. 6B is a graphical view of a background signal spectrogram.

In addition to the negative effects caused by collateral scattered light discussed previously, spectrographic measurements are further obscured by what is known as a dark signal. The dark signal is generated by the photosensor array during any measurement, even if the laser source is turned off or is blocked from interaction with any gas in the chamber. It should be briefly noted that intensity of the dark signal is unrelated to either the power of the laser beam used or to the number density of gas disposed within the chamber. In the preferred embodiment, a dark signal spectrogram representative of the dark signal alone is generated by the system with the laser source turned off (block 314 of FIG. 3). The dark signal spectrogram is then stored in the memory of the computation device, for further use in calibration. FIG. 6A is a graphical view showing the dark signal spectrogram 601. The intensity of the dark signal spectrogram measured at the ith frequency can be expressed using vector notation as $b_{Di}$. Using the dark signal spectrogram and the first and second normalized spectrograms, the computation means generates a background signal spectrogram in accordance with block 316 of the flow chart shown in FIG. 3. and using the equation:

$$b_{Bi} = (N_1(b_{2i} - b_{Di}) - N_2(b_{1i} - b_{Di}))/(N_1 - N_2)$$

where $b_{Bi}$ represents intensity of the background signal spectrogram at the ith frequency, $N_1$ represents the first number density level generated previously, and $N_2$ represents the second number density level generated previously. The background signal spectrogram and the dark signal spectrogram are included in the operating parameter of the system, which in turn is used during normal operation of the system after calibration is complete to subtract the background signal spectrogram and the dark signal spectrogram from any measured spectrogram.

Figure 7A:
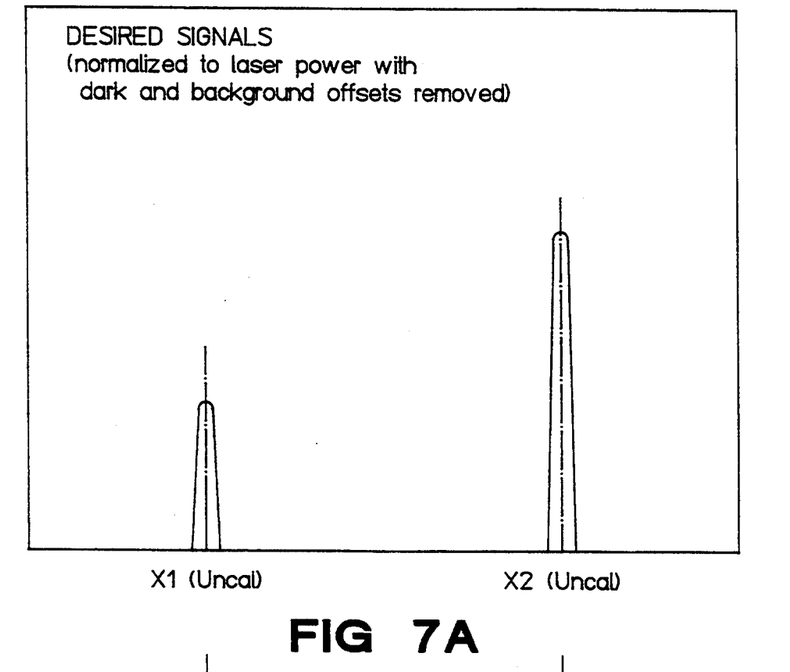
FIG. 7A is a graphical view of a measured spectrogram due to air alone.

During field calibration, the computation means generates a measured spectrogram due to air alone by subtracting the background signal spectrogram and the dark signal spectrogram from the first normalized spectrogram. This is expressed by the equation:

$$b_{i,AIR} = b_{1i} - b_{Di} - b_{Bi}$$

where $b_{i,AIR}$ represents intensity at the ith frequency of the measured spectrogram due to air alone. FIG. 7A is a graphical view of the measured spectrogram due to air alone. It should be briefly noted that beneficial results can also be achieved when the second normalized spectrogram is alternatively used, in place of the first normalized spectrogram, to generate the measured spectrogram due to air alone.

Figure 7B:
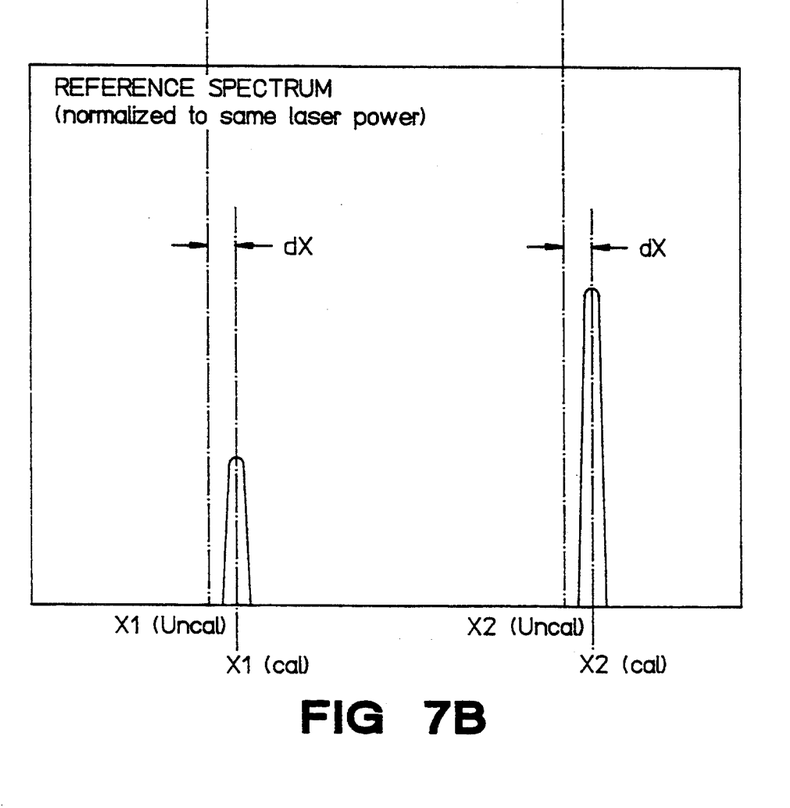
FIG. 7B is a graphical view of a calibrated standard spectrogram.

In accordance with block 318 of the flow chart shown in FIG. 3, a calibrated standard spectrogram comprising spectral data stored in the memory device of the computation means is retrieved. FIG. 7B is a graphical view of the calibrated standard spectrogram. It should be briefly noted that such spectral data is generated during factory calibration of the system, and is stored for use during field calibration of the system.

In contrast to the uncalibrated frequency locations of the spectral peaks along the horizontal axis of the measured spectrogram due to air alone shown in FIG. 7A, the frequency locations of the spectral peaks along the horizontal axis of the calibrated standard spectrogram shown in FIG. 7B are shown as being calibrated, using the abbreviation "Cal". If the calibrated standard spectrogram of FIG. 7B is compared to the measured spectrogram due to air alone of FIG. 7A, the figures show that there is a horizontal offset, dX, between the uncalibrated frequency locations of the spectral peaks along the horizontal axis of FIG. 7A and the calibrated frequency locations of the spectral peaks along the horizontal axis of FIG. 7B.

Figure 8A:
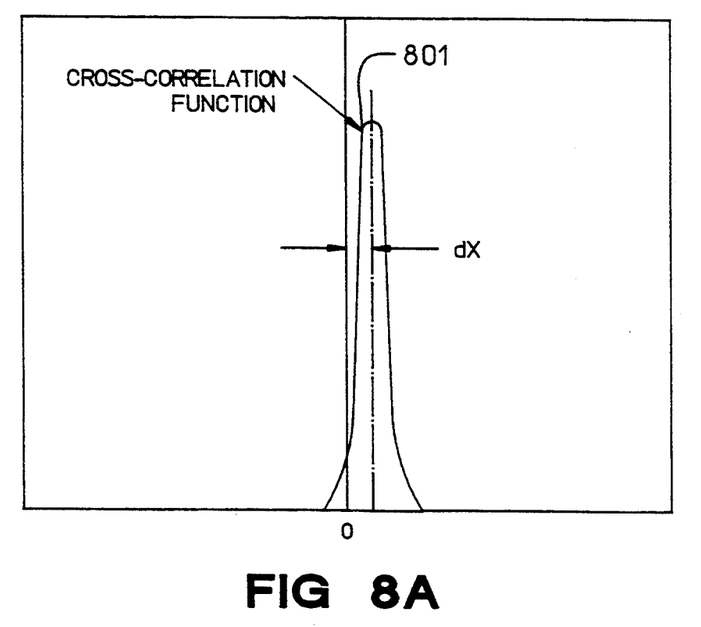
FIG. 8A is a graphical view of a cross correlation of the measured spectrogram due to air alone, as shown in FIG. 7A, and the calibrated standard spectrogram, as shown in FIG. 7B.

In the preferred embodiment, the computation means generates a cross correlation of the calibrated standard spectrogram of air and the measured spectrogram due to air alone, as shown in FIG. 8A. The cross correlation function 801 provides a measure of the horizontal offset, dX discussed previously. In accordance with block 320 of FIG. 3, the computation means generates and stores in the memory a frequency location alignment parameter that is based on the measure of the horizontal offset, dX. The frequency location alignment parameter is included in the operating parameter of the system, which in turn is used during normal operation of the system after calibration to correctly align any measured spectrogram. As indicated previously, the respective spectral peaks of oxygen and nitrogen are especially useful as calibration points because they are separated by a broad frequency range. Accordingly, using air in calibration is an effective choice because spectrograms of air provide a broad useful calibration range between calibration points.

During field calibration, the measured spectrogram due to air alone is correctly aligned using the frequency location alignment parameter. Accordingly, vector notation is used in the expression $b_{i+j,AIR}$, which represents the intensity of the measured spectrogram due to air alone at a frequency that is shifted from the ith frequency by an amount j, wherein j corresponds to the frequency location alignment parameter.

In accordance with block 322 of the flow chart shown in FIG. 3, the computer means generates a gain parameter. The intensity of the aligned measured spectrogram due to air alone is scaled by the gain parameter to match the intensity of the standard spectrogram. The relationship between these two spectrograms is expressed using vector notation by the equation:

$$b_{i,STD} = g \cdot (b_{i+j,AIR})$$

where $b_{i,STD}$ is the intensity of the standard spectrogram and g is the gain parameter. The gain parameter is included in the operating parameter of the system, which in turn is used during normal operation of the system after calibration to correctly scale intensity of any given measured spectrogram.

Figure 8B:
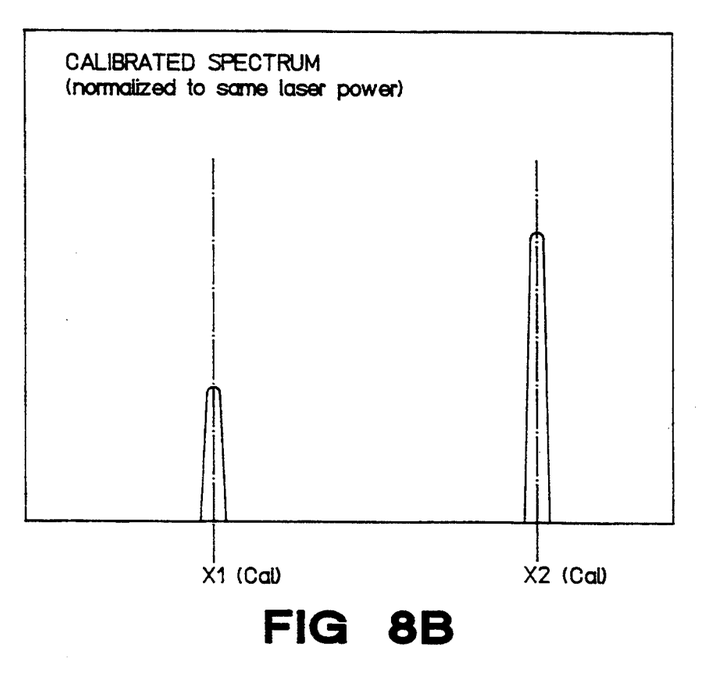
FIG. 8B is a graphical view of a correctly calibrated spectrogram.

In accordance with block 324 the flow chart of FIG. 3, calibration is completed by setting the operating parameter of the system. This is achieved by storing the operating parameter in the memory device of the computation means for later use as previously described. For example, FIG. 8B shows a correctly calibrated spectrogram generated using the operating parameter.

ALTERNATIVE EMBODIMENT

Figure 9:
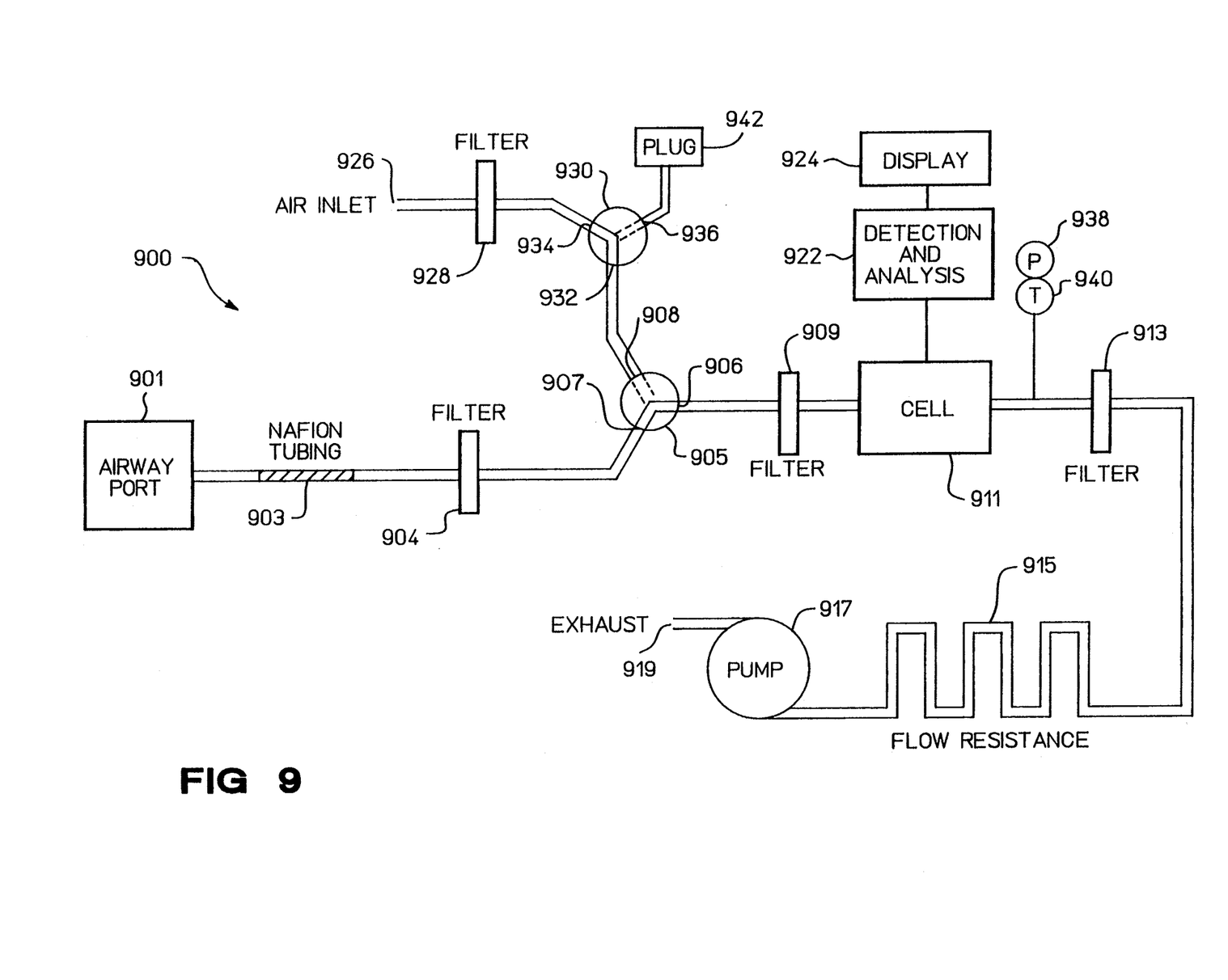
FIG. 9 is a block diagram of an alternative spectrographic analysis system used in conjunction with an alternative embodiment of the method of the invention.

FIG. 9 shows an alternative spectrographic analysis system 900 used in conjunction with an alternative embodiment of the present invention. During normal operation of the alternative spectrographic analysis system, an airway port 901 conducts a flow of breath, exhaled by a surgical patient, into the system. The flow of breath passes through a length of Nafion tubing 903, which is selectively permeable to water vapor and is coupled to the airway port to remove moisture in the breath.

A first filter 904 is coupled to the Nafion tubing 903. A first valve 905 has an outlet 906 and a pair of alternatively selectable inlets 907, 908. A first member 907 of the pair of inlets is coupled to the first filter. During normal operation, only the first member 907 of the pair of inlets is selected, thereby conducting the flow of breath into the system and through the first valve. The outlet 906 of the first valve is coupled to a chamber 911 of a sampling cell by means of a second filter 909. A flow resistance device 915 is coupled to the chamber of the sampling cell by means of a third filter 913. A pump 917 is coupled to the flow resistance device so as to draw the flow of breath through the system. The flow of breath is conducted out of the system through an exhaust 919 coupled to the pump.

The flow of breath is received by the chamber of the sampling cell and analyzed by employing the Raman-effect. In a similar manner as discussed previously with respect to the preferred embodiment, a laser (not shown in FIG. 9) illuminates breath disposed within the chamber to generate a spectral signal by the Raman-effect.

As in the preferred spectrographic analysis system discussed previously, the alternative spectrographic analysis system includes a detection and analysis portion 922 optically coupled to the chamber by means of collection optics. As discussed previously, the detection and analysis portion is essentially a spectrometer including a diffraction grating, a photosensor array, and a computation means programmed to generate a spectrogram. The computation means includes a microprocessor coupled to a suitable memory device. The detection and analysis portion 922 operates in a similar manner as discussed previously to produce a spectrogram of the breath. To display the resulting spectrogram, a display device 924 is coupled to the detection and analysis portion of the alternative spectrographic analysis system.

Figure 10:
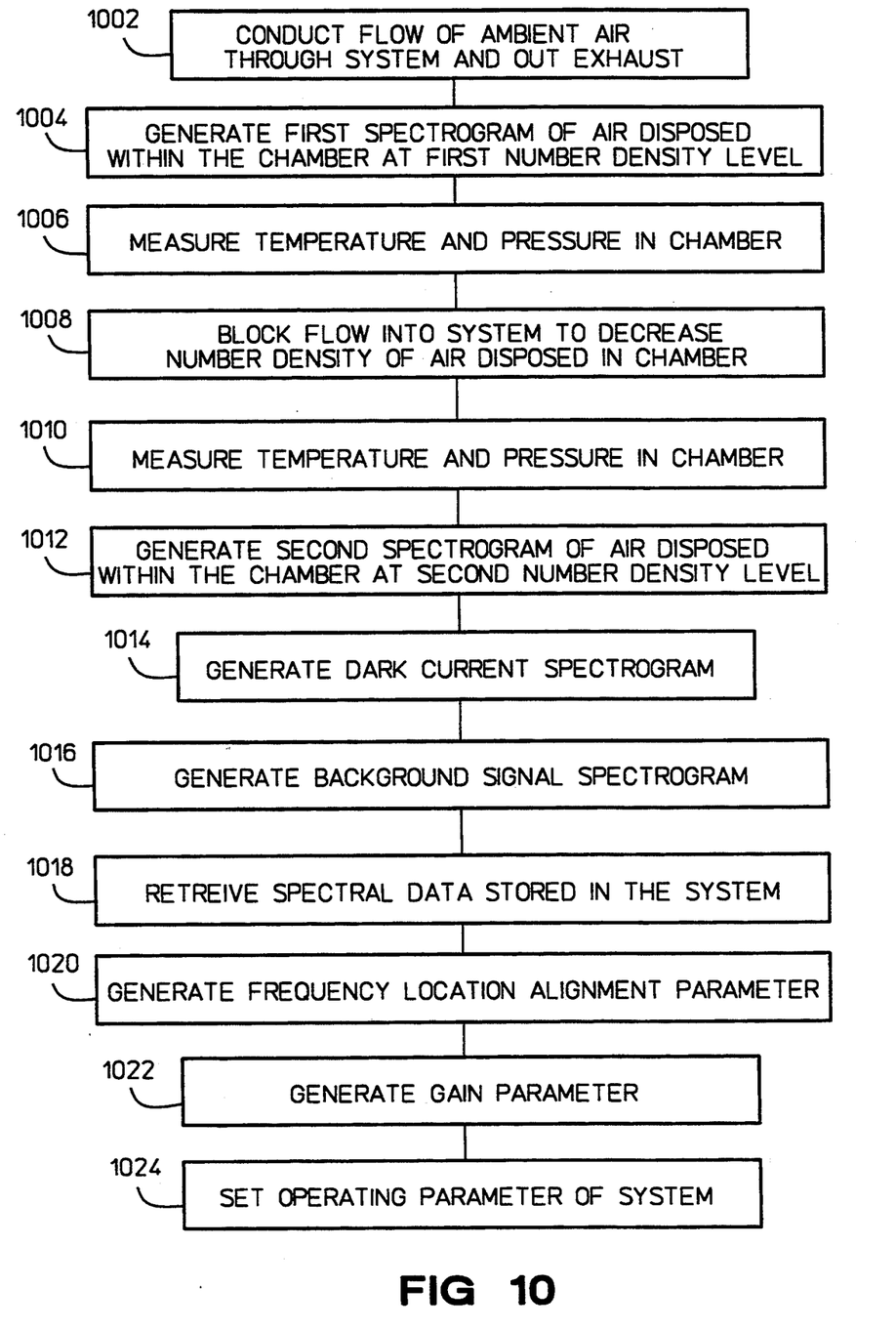
FIG. 10 is a flow chart shown illustrating an alternative embodiment of the method of the present invention.

In order to prepare the alternative spectrographic analysis system for normal operation as discussed, a field calibration is performed according to the alternative embodiment of the calibration method of the present invention. A flow chart shown in FIG. 10 illustrates the alternative embodiment of the calibration method of the present invention. In accordance with block 1002 of the flow chart of FIG. 10, ambient air is conducted through the analysis system and out the exhaust. This is easily illustrated using the block diagram of FIG. 9.

As shown in FIG. 9, ambient air is collected through an ambient air inlet 926, which is coupled to a fourth filter 928. A second valve 930 has an outlet 932 and a pair of alternatively selectable inlets 934, 936. The fourth filter 928 is coupled to a first member 934 of the pair of inlets of the second valve 930.

Initially, the first member 934 of the pair of inlets of the second valve is selected so as to conduct ambient air through the second valve. The outlet of the second valve is coupled to a second member 908 of the pair of inlets of the first valve. During the alternative calibration method, the second member 908 of the pair of inlets of the first valve is selected so that only ambient air flows though the first valve.

The pump 917 draws a flow of ambient air through the system, and in particular through the chamber of the sampling cell. The flow of ambient air is disposed within the chamber 911 of the sampling cell at a first number density level.

In a similar manner as previously discussed with respect to the preferred embodiment, the Raman-effect is employed to generate a spectral signal from the flow of ambient air. In a similar manner as previously discussed, the spectral signal is collected from the chamber by the collection optics and analyzed by the detection and analysis portion of the system to produce a first measured spectrogram of the ambient air disposed within the chamber at the first number density level (block 1004 of FIG. 10).

A cell pressure sensor 938 and a cell temperature sensor 940 are each coupled to the sampling cell and are adapted for sensing the pressure and temperature of any gasses disposed within the chamber of the cell. In accordance with block 1006 of the flow chart of FIG. 10, the cell pressure and temperature sensors measure the pressure and temperature of the air disposed within the chamber at the first number density level. The computation means receives these measurements of pressure and temperature and uses them in conjunction with the ideal gas law to generate a value $N_1$ which represents the first number density level.

In accordance with block 1008 of the flow chart of FIG. 10, the flow of ambient air into the system is blocked to decrease number density of air disposed in the chamber. The flow is blocked by selecting a second member 936 of the pair of inlets of the second valve 930, while the second member 908 of the pair of inlets of the first valve 905 is still selected. A plug 942 is coupled to the second member 936 of the pair of inlets of the second valve to block any flow into the second valve when the second member 936 is selected, thereby interrupting the flow of ambient air into the system.

While the flow of ambient air into the system is interrupted, the pump 917 continues to pump air out of the chamber to exit the system through the exhaust, thereby decreasing the amount of air disposed within the chamber of the cell. In this way, the air is partially evacuated from the chamber. Accordingly, the first number density level of air disposed within the chamber of the cell changes to a second number density level. For the alternative embodiment, it is preferred that the second number density level be significantly smaller than the first number density level so as to reduce undesirable effects of errors inherent in the pressure sensor. For example, as discussed previously, if a commonly available silicon pressure sensor is used, such a sensor has an accuracy of about 0.1%. A 25% difference between the first and second number density levels reduces undesirable effects of errors in measurements made by the silicon pressure sensor.

In accordance with block 1010 of the flow chart shown in FIG. 10, the cell pressure and temperature sensors measure the pressure and temperature of the air disposed within the chamber at the second number density level. The computation means receives these measurements of pressure and temperature and uses them in conjunction with the ideal gas law to generate a value $N_2$ which represents the second number density level.

By monitoring changes in temperature and pressure, the computation means indirectly monitors changes in the number density of the air disposed within the chamber of the cell. When measurements made by the cell pressure and temperature sensors indirectly indicate that the density of air within the chamber is at the second number density level, a spectral signal from the air disposed within the cell is generated and analyzed, in a similar manner as discussed previously with respect to the preferred embodiment. The detection and analysis portion of the system analyzes the spectral signal to produce a second measured spectrogram of the air at the second number density level (block 1012 of FIG. 10).

In general, the intensity of the spectral signal produced by the Raman effect is decreased as the number density of the illuminated gas is decreased. Accordingly, for the alternative embodiment of the calibration method, the second number density is significantly smaller than the first number density, and therefore the intensity of spectral peaks in the second measured spectrogram is significantly smaller than the intensity of spectral peaks in the first measured spectrogram. In a similar manner as previously discussed with respect to the preferred embodiment, the first and second measured spectrograms are normalized to produce a first and second normalized spectrogram.

In a similar manner as discussed previously, a dark current spectrogram is generated (block 1014 of FIG. 10). Using the dark signal spectrogram and the first and second normalized spectrogram, the computation means generates a background signal spectrogram in accordance with block 1016 of the flow chart shown in FIG. 10, in a similar manner as discussed previously. Spectral data stored in the memory of the system is retrieved (block 1018), a frequency location alignment parameter and a gain parameter are generated (blocks 1020 and 1022), and an operating parameter of the system are set, all in a similar manner as discussed previously.

The embodiments of the present invention discussed herein provide for efficient field calibration of a system adapted for spectrographic analysis of gaseous substances. Because the embodiments discussed herein employ an easily available gas, such as ambient air, the present invention provides for field calibration of the system without need for premeasured bottles of specialized calibration gasses. As was discussed herein, the method of the present generates spectrograms from the easily available gas at various number density levels of the gas, thereby completing field calibration of the system without the expense and inconvenience associated with methods that employ purified samples of noble gases.

While the invention has been described in detail herein in accord with certain preferred embodiments thereof, many modifications and changes therein may be effected by those skilled in the art. Accordingly, it is intended by the appended claims to cover all such modifications and changes as fall within the true spirit and scope of the invention.

What is claimed is:

1. A method for calibrating a system adapted for spectrographic analysis of gaseous substances, comprising the steps of:
   using the system to generate a first spectrogram from air at a first number density level;
   using the system to generate a second spectrogram from air at a second number density level;
   using the first and second spectrogram of air to generate a background signal spectrogram;
   retrieving spectral data stored in the system; and
   using the background signal spectrogram, one of the spectrograms of air, and the retrieved spectral data to set an operating parameter of the system.

2. A method as in claim 1 wherein the step of generating the first spectrogram from air includes the steps of:
   collecting ambient air;
   disposing the collected air within a chamber;
   stimulating the air disposed within the chamber to produce a spectral signal; and
   detecting the spectral signal to produce the first spectrogram.

3. A method as in claim 1 wherein the operating parameter of the system includes a frequency location alignment parameter.

4. A method as in claim 1 wherein the operating parameter of the system includes a gain parameter of the system.

5. A method as in claim 3 wherein the operating parameter of the system further includes a gain parameter of the system.

6. A method for calibrating a system adapted for spectrographic analysis of gaseous substances, comprising the steps of:
   generating a first spectrogram from a gas at a first number density level;
   changing density of the gas from the first number density level to a second number density level;
   generating a second spectrogram of the gas at the second density level; using the first and second spectrogram to set an operating parameter of the spectrographic system.

7. A method as in claim 6 wherein the step of using the first and second spectrogram to set an operating parameter of the spectrographic system includes the steps of:
   using the first and second spectrogram to generate a background signal spectrogram; and
   using the background signal spectrogram in setting the operating parameter of the spectrographic system.

8. A method as in claim 6 wherein the operating parameter of the spectrographic system includes a frequency location alignment parameter.

9. A method as in claim 6 wherein the operating parameter of the spectrographic system includes a gain parameter.

10. A method as in claim 6 wherein the second number density level differs from the first number density level by at least twenty five percent.

11. A method as in claim 6 wherein the step of changing density of the gas includes disposing the gas within a chamber so that the gas is at the second number density level.

12. A method as in claim 6 wherein the step of generating the first spectrogram includes:
    disposing the gas within a chamber so that the gas is at the first number density level;
    stimulating the gas to produce a spectral signal; and
    detecting the spectral signal to produce the first spectrogram.

13. A method as in claim 12 wherein the step of changing density of the gas includes partially evacuating the gas from the chamber, thereby changing density of the gas in the chamber from the first number density level to the second number density level.

14. A method as in claim 12 wherein the step of changing density of the gas includes disposing more of the gas within the chamber, thereby changing density of the gas in the chamber from the first number density level to the second number density level.

15. A method as in claim 6 wherein the gas is a mixture of constituent gasses.

16. A method as in claim 15 wherein the mixture of constituent gases is air.

17. A method as in claim 6 wherein the gas at the first number density level is ambient air.

18. A method as in claim 6 wherein the first and second spectrograms are generated by means of Raman spectroscopy.

19. A method as in claim 8 wherein the operating parameter of the system further includes a gain parameter of the system.

20. An apparatus for calibrating a system adapted for spectrographic analysis of gaseous substances, the apparatus comprising:

means coupled with the system for generating a first spectrogram from a gas at a first number density level;

means coupled with the system for changing density of the gas from the first number density level to a second number density level;

means coupled with the system for generating a second spectrogram of the gas at the second density level; and means using the first and second spectrogram for setting an operating parameter of the spectrographic system.

* * * * *